United States Patent [19]
Ramirez et al.

[11] Patent Number: 6,096,702
[45] Date of Patent: Aug. 1, 2000

[54] POST FOAMING CLEAR GELS AND SOLUTIONS

[75] Inventors: Jose E. Ramirez, Trumbull; Mohan Vishnupad, Monroe, both of Conn.

[73] Assignee: Imaginative Research Associates, Inc., Milford, Conn.

[21] Appl. No.: 09/164,905

[22] Filed: Oct. 1, 1998

[51] Int. Cl.$^7$ .............................. C11D 17/08; A61K 7/11
[52] U.S. Cl. .................. 510/421; 510/119; 510/123; 510/125; 510/127; 510/128; 510/131; 510/137; 510/159; 510/387; 510/499; 510/506; 424/70.11; 424/70.21
[58] Field of Search .............................. 424/70.11, 70.21; 510/119, 123, 125, 127, 128, 130, 131, 137, 158, 159, 382, 387, 499, 506, 421

[56] References Cited

U.S. PATENT DOCUMENTS

| | | | |
|---|---|---|---|
| 2,995,521 | 8/1961 | Bluard | 424/401 |
| 3,959,160 | 5/1976 | Horsler et al. | 252/90 |
| 4,240,450 | 12/1980 | Grollier et al. | 132/7 |
| 4,252,656 | 2/1981 | Liebowitz et al. | 252/8.8 |
| 4,438,009 | 3/1984 | Brusky et al. | 252/90 |
| 4,652,389 | 3/1987 | Moll | 252/90 |
| 4,726,944 | 2/1988 | Osipow et al. | 424/70 |
| 4,744,979 | 5/1988 | Osipow et al. | 424/73 |
| 4,761,273 | 8/1988 | Grollier et al. | 424/47 |
| 4,772,427 | 9/1988 | Dawson et al. | 252/559 |
| 4,780,100 | 10/1988 | Moll | 8/137 |
| 4,931,204 | 6/1990 | Ramirez et al. | 252/167 |
| 4,976,953 | 12/1990 | Orr et al. | 424/47 |
| 5,091,111 | 2/1992 | Neumiller | 252/305 |
| 5,116,606 | 5/1992 | Alt | 424/70 |
| 5,145,604 | 9/1992 | Neumiller | 252/312 |
| 5,186,857 | 2/1993 | Ramirez et al. | 252/167 |
| 5,248,495 | 9/1993 | Patterson et al. | 424/73 |
| 5,254,334 | 10/1993 | Ramirez et al. | 424/70 |
| 5,429,815 | 7/1995 | Faryniarz et al. | 424/47 |
| 5,540,853 | 7/1996 | Trinh et al. | 510/101 |
| 5,635,469 | 6/1997 | Fowler et al. | 510/406 |
| 5,756,439 | 5/1998 | He et al. | 510/159 |
| 5,849,310 | 12/1998 | Trinh et al. | 424/401 |
| 5,861,145 | 1/1999 | Lucas et al. | 424/65 |

FOREIGN PATENT DOCUMENTS 0453238  10/1991  European Pat. Off. .

OTHER PUBLICATIONS

Product Literature for BASF Performance Chemicals: Pluronic® & Tetronic® Surfactants, 1996 no month given.
Product Literature for Probutyl DB–10, Croda Formulary, pp. 6–12 (1996 update) no month given.

*Primary Examiner*—Yogendra Gupta
*Assistant Examiner*—Brian P. Mruk
*Attorney, Agent, or Firm*—Dilworth & Barrese

[57] ABSTRACT

Novel clear solutions or gels containing a volatile hydrocarbon, surfactants and a polyalkylene oxide block copolymer coupling agent do not separate, but rather due to solubilization of the volatile hydrocarbon by the coupling agent, provide acceptable consumer products.

20 Claims, No Drawings

POST FOAMING CLEAR GELS AND SOLUTIONS

BACKGROUND

1. Technical Field

The present disclosure relates to post-foaming detergent compositions. More specifically, the present disclosure relates to compositions containing coupling agents selected from a group of polyalkylene oxide block copolymer surfactants, which in the presence of anionic and amphoteric detergents solubilize a volatile hydrocarbon producing a clear solution or gel. These self-foaming solutions or gels can be useful as a skin cleanser, hair shampoo or shower gel. They also have application as household cleaners such as spot cleansers for clothes, carpet cleaner or hard surface cleaner.

2. Background of the Related Art

U.S. Pat. No. 5,429,815, discloses an optional use of coupling agent such as propoxylated adduct of mono or polyhydric alcohols to prepare stable, single phase self-foaming cleanser.

U.S. Pat. No. 4,726,944 discloses clear shampoo formulations which are aqueous solutions of water-soluble salts of lauryl sulfate, volatile hydrocarbon, a tertiary amine oxide and water soluble gums.

In U.S. Pat. No. 4,744,979 a clear formulation is provided by using aqueous soap solution and a surface active agent such as amine oxide or alkanolamides and a volatile water-soluble organic liquid.

U.S. Pat. No. 4,772,427 achieves a clear solubilized volatile hydrocarbon formulation by using water soluble anionic alkali metal $C_{10}$–$C_{16}$ alkyl ether sulfate, water dispersible ethoxylated fatty alcohol or fatty ester, isopropyl myristate, mono- or disaccharide and a blend of volatile hydrocarbons such as n-pentane and isobutane. However, U.S. Pat. No. 4,772,427 states at column 6, line 20–27 that "the omission of a single component adversely effects the unique properties of the total composition. Accordingly the criticality of the essential ingredients and the specificity of each ingredients is necessary in the formulation . . . " of the post-foaming shower gel products disclosed therein.

In U.S. Pat. No. 5,186,857, an oil in water emulsion composition includes foaming surfactants that are utilized to increase solubility of a volatile hydrocarbon.

SUMMARY

All the above mentioned post-foaming potential technology make use of ethoxylated or propoxylated coupling agents to solubilize volatile hydrocarbon to prepare post foaming liquids.

For the first time ever, it has been discovered that block polymers containing both ethoxylation and propoxylation in one molecule, e.g., Pluronic-type or Tetronic-type surfactants, can be used to solubilize a volatile hydrocarbon (such as n-pentane, isopentane, n-butane, isobutane and $C_1$–$C_6$ alkylethers such as dimethyl ether, diethyl ether, methyl ether and diisobutane ether) in anionic and amphoteric detergent solutions.

The resulting clear, instant foaming liquid or gel will foam on a surface with or without the aid of water. The clear solution or gel will not self-foam when enclosed in a bottle and exposed to high temperature such as 100–120° F. Accordingly, products made from the present compositions are consumer friendly and can withstand transportation and storage condition en route to market place. The instant foaming clear solutions or gels described herein can be packaged in an unpressurized container such as bottle and pumps or in pressurized aerosol packages when n-butane, isobutane or dimethyl ether propellant is used.

In another aspect, novel compositions containing ammonium cocoyl isethionate in combination with an amphoteric surfactant are disclosed herein. This combination is particularly useful in skin and hair care compositions due to the extremely mild properties of these surfactants.

DETAILED DESCRIPTION OF PREFERRED EMBODIMENTS

Compositions and products in accordance with this disclosure contain a primary surfactant or combination of primary surfactants, optionally a secondary surfactant, water, a volatile hydrocarbon, and a coupling agent to solubilize the volatile hydrocarbon.

The surfactant or combination of surfactants should be soluble in water to produce a clear solution or gel. Suitable primary surfactant include anionic surfactants such as, for example, alkyl ether sulfates, alkyl sulfates, ammonium cocoyl isethionate, and amphoteric surfactants.

The amount of primary surfactant employed in this composition will depend on a number of factors including the end use of the composition, the desired foaming characteristics and the other ingredients present in the composition. A combination of primary surfactants can also be employed to formulate a desired product having particular characteristics.

Additionally, a unique combination of ammonium cocoyl isethionate with amphoteric surfactants has been found to solubilize volatile hydrocarbons to produce clear post-foaming solutions without the aid of any ethoxylated, propoxylated or mixed block polymer. Preferably, the amphoteric surfactant is a betaine. Suitable betaines include cocoamidopropyl betaine, behenyl betaine and babassuamido propyl betaine which are commercially available under the INCRONAM trade name from Croda Formulary, Parsippany, N.J.

A volatile hydrocarbon is included in the present compositions to provide foaming upon use or as a propellant. The volatile hydrocarbon is used to enhance the foam produced by the primary surfactant(s) and is a gas producing agent, which when exposed to air and ambient temperature will provide instant, copious lather. The volatile organic liquid foam enhancing agent preferably boils in the range of 25° C. to 50° C. at atmospheric pressure. Such volatile organic liquids include saturated hydrocarbons such as n-pentane, iso-pentane, n-butane, isobutane and $C_1$–$C_6$ alkyl ethers such as dimethyl either, diethyl ether, methylethyl ether and diisopropyl ether. The amount of volatile hydrocarbon in the compositions will depend upon the type of product being formulated and the function to be served by the volatile hydrocarbon. Normally, however, the volatile hydrocarbon will be present in the amount from about 1 to about 7 weight percent by weight of the final composition, preferably from about 3 to about 4 weight percent.

The present compositions also contain an effective solubilizing amount of a coupling agent. The coupling agents used in the novel compositions described herein are polyalkylene oxide block copolymer surfactants. Particularly useful are compounds containing both polyoxyethylene and polyoxypropylene blocks. Most preferred polyalkylene oxide block copolymers useful herein are those available under the PLURONIC or TETRONIC trade names from BASF Corporation, Mount Olive, N.J. These compounds are quite different compounds from conventional ethoxylated or propoxylated coupling agents disclosed in prior art post-foaming cleaners.

Pluronic-type surfactants contain alternating blocks of polyethylene oxide and polypropylene oxide. Typically, Pluronic-type surfactants are prepared by first making a hydrophobe of desired molecular weight by the controlled addition of propylene oxide to the two hydroxyl groups of propylene glycol. Ethylene oxide is then added to sandwich this hydrophobe between hydrophilic groups, the structure of Pluronic-type surfactants where propylene oxide is sandwiched between ethylene oxide as shown below.

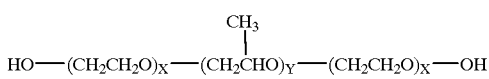

Another Pluronic-type surfactant known generally as Pluronic R surfactants have the hydrophobic and hydrophilic blocks reversed. Thus, Pluronic R surfactants have a structure as follows:

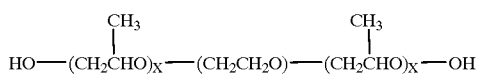

Tetronic-type surfactants are another class of coupling agents useful herein. Tetronic-type surfactants are tetrafunctional block copolymers derived from the sequential additional of propylene oxide and ethylene oxide to ethylenediamine. Tetronic-type surfactants thus have the general formula

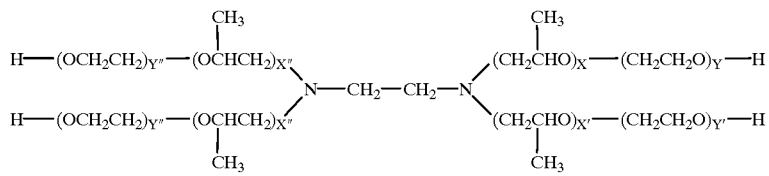

The Tetronic R surfactant are produced by the sequential addition of ethylene oxide and propylene oxide to ethylene diamine. The general structure of Tetronic R surfactants is:

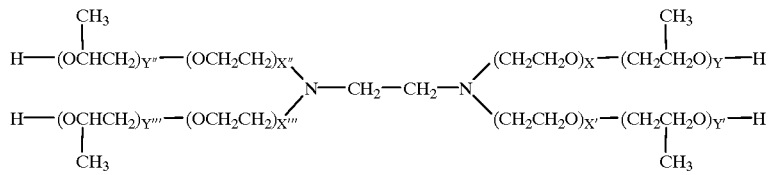

An effective solubilizing amount is an amount sufficient to prevent any significant separation of the volatile hydrocarbon from the surfactant. Thus, for example, an effective amount will prevent the formation of a separate layer of the volatile hydrocarbon. Typically, an effective solubilizing amount will be from about 0.5 to about 20 percent by weight of the final composition, preferably about 5 to about 10 weight percent.

Water (preferably deionized) in an amount from about 10 to about 65 percent by weight of the final composition is also present in the novel compositions described herein.

In addition to the above-mentioned ingredients, the present instant foaming clear aqueous solution or gel may also contain a variety of non-essential ingredients. For example, water soluble gums, such as cellulosic polymers or natural gum, or water soluble cleaners can be added impart desired aesthetic properties to the product. The clear gels and solutions may also contain humectant such as glycerin, sorbitol, propylene glycol etc. which provide moisturizing benefit to the skin or hair. Fragrance and color can be added to improve the cosmetic appearance of the product. Active ingredients such as triclosan, chlorohexidene gluconate or salicylic acid can also be dissolved in the surfactant system to provide an anti-bacterial functional product. Furthermore, small amounts of water soluble soaps such as palmitate or stearate of sodium/potassium or ammonium can be used to improve the foam stability for a shaving application. Similarly alkanolamide can be added to improve foam stability.

The clear solution or gel compositions achieved by means of a polyalkylene oxide coupling agent such as a Pluronic or Tetronic-type block polymer and mild surfactant concentration of ammonium cocoyl isethionate and amphoteric surfactant can be packaged in any conventional non-pressurized glass or plastic bottle. In cases where isobutane or dimethyl ether is used as a post-foaming solvent, a pressurized spray bottle or a pressurized barrier package is preferably used.

EXAMPLE

The following examples are presented to illustrated specific embodiments of the present compositions and methods. These examples should not be interpreted as limitations upon the scope of the invention. Comparative examples are also presented to show the novel effects provided by the present compositions. All values shown in Tables I–V are weight percent based on the total weight of the composition.

Comparative Examples A–C

TABLE I

|  | Ex. A | Ex. B | Ex. C |
|---|---|---|---|
| Sodium alkyl ether sulfate (30% actives) | 30 | — | 30 |
| cocoamidopropyl betaine (30% actives) | 10 | 30 | — |
| Water | 57 | 67 | 67 |
| N-pentane | 3 | 3 | 3 |

The compositions of Comparative Examples A, B and C which contain no block copolymer surfactant as a coupling agent, showed n-pentane separation at the top of the bottle in less than 24 hours. These Comparative Examples clearly indicate that n-pentane is insoluble in a primary surfactant or a mixture of the primary surfactant and an amphoteric surfactant.

Examples 1–7

Compositions having the formulations given in Table II were prepared to show the effect of including a Pluronic-type surfactant as a coupling agent in a composition containing a combination of anionic and amphoteric surfactants.

TABLE II

|  | Ex. 1 | Ex. 2 | Ex. 3 | Ex. 4 | Ex. 5 | Ex. 6 | Ex. 7 |
| --- | --- | --- | --- | --- | --- | --- | --- |
| Sodium lauryl ether sulfate (28% actives) | 30 | 30 | 30 | 30 | 30 | 30 | 30 |
| cocoamidopropyl betaine (30% actives) | 10 | 10 | 10 | 10 | 10 | 10 | 10 |
| Pluronic L-43 | 5 | — | — | — | — | — | 10 |
| Pluronic F-61 | — | 5 | — | — | — | — | — |
| Pluronic 31 RI | — | — | 5 | — | — | — | — |
| Pluronic 17 R2 | — | — | — | 5 | — | — | — |
| Pluronic L-10 | — | — | — | — | 5 | — | — |
| Pluronic L-101 | — | — | — | — | — | 5 | — |
| Pluronic F-68 | — | — | — | — | — | — | 5 |
| Water | 52 | 52 | 52 | 52 | 52 | 52 | 52 |
| n-pentane | 3 | 3 | 3 | 3 | 3 | 3 | 3 |

The compositions in Table II produce a clear liquid or a gel without any layer separation. When kept at room temperature or at higher temperature such as 110°–120° F., these compositions stay clear without any separation, indicating that complete solubilization of the volatile hydrocarbon in the anionic and amphoteric surfactants has been achieved with the aid of the coupling agent.

Overnight standing at room temperature or in an oven at 100–200° F. will clear any air bubbles in the composition that might form during mixture of the product. The end product is a clear solution where a coupling agent is used. This is quite a surprising result when compared to the distinct separate layer of n-pentane that forms where no coupling agent is used as in the formulations of Comparative Examples A to C in Table I.

Examples 8–13

Additional formulations as shown in Table III were prepared to show the solubilizing effect of Pluronic-type surfactants in a composition wherein an amphoteric surfactant is used alone as the primary surfactant.

TABLE III

|  | Ex. 8 | Ex. 9 | Ex. 10 | Ex. 11 | Ex. 12 | Ex. 13 |
| --- | --- | --- | --- | --- | --- | --- |
| cocoamidopropyl betaine (30% actives) | 30 | 30 | 30 | 30 | 30 | 30 |
| Pluronic L-43 | 20 | — | — | — | — | — |
| Pluronic L-61 | — | 20 | — | — | — | — |
| Pluronic L-101 | — | — | 20 | — | — | — |
| Pluronic L-10 | — | — | — | 20 | — | — |
| Pluronic 31 R1 | — | — | — | — | 20 | — |
| Pluronic 17 R2 | — | — | — | — | — | 20 |
| Water | 47 | 47 | 47 | 47 | 47 | 47 |
| n-pentane | 3 | 3 | 3 | 3 | 3 | 3 |

The formulations of Examples 8–13 all stayed in one phase as a clear solution without any separation at room temperature or at 120° F., indicating that the Pluronic-type surfactant has solubilized the pentane in the amphoteric surfactant system. As shown by Comparative Example B in Table I, the amphoteric surfactant alone did not solubilize pentane, resulting in phase separation.

Examples 14 and 15

The formulations shown in Table IV were prepared and the resulting compositions observed to determine whether pentane separation occurs.

TABLE IV

|  | Ex. D | Ex. 14 | Ex. 15 |
| --- | --- | --- | --- |
| Ammonium Cocoyl Isethionate (30% actives) | 30 | 30 | 30 |
| cocoamidopropyl betaine (30% actives) | — | 20 | 20 |
| Pluronic F-98 | — | 10 | — |
| Water | 67 | 37 | 47 |
| pentane | 3 | 3 | 3 |

Comparative Example D which contained an anionic surfactant and no coupling agent showed pentane separation at the top within 24 hours. Example 14 provided a one-phase clear solution showing the solubilizing effect Pluronic-type surfactants. Quite surprisingly, however, Example 15 also remained as a one-phase clear solution despite the absence of a Pluronic-type coupling agent. Example 15 demonstrates the unexpected pentane solubilizing effects of the combination of a particular anionic surfactant, i.e., ammonium cocoyl isethionate with an amphoteric surfactant such as a betaine.

Examples 16–19

The formulations shown in Table V were prepared to show the solubilizing effects of Tetronic-type surfactants.

TABLE V

|  | Ex. 16 | Ex. 17 | Ex. 18 | Ex. 19 |
| --- | --- | --- | --- | --- |
| Sodium Alkyl Ether Sulfate (28% actives) | 30 | 30 | 30 | 30 |
| cocoamidopropyl betaine (30% actives) | 10 | 10 | 10 | 10 |
| Tetronic 150 RT | 5 | — | — | — |
| Tetronic 1301 | — | 5 | — | — |
| Tetronic 904 | — | — | 5 | — |
| Tetronic 701 | — | — | — | 5 |
| Water | 52 | 52 | 52 | 52 |
| Pentane | 3 | 3 | 3 | 3 |

Examples 16–19 once again show complete solubilization of n-pentane using a polyalkylene oxide copolymer coupling agent to produce a clear solution with no layer separation. In comparison, as shown by Comparative Examples A, B, C in Table I, without the block polymer coupling agent, n-pentane separated into a top layer indicating insolubility in the same surfactant system.

We claim:

1. A single phase composition comprising:
   a surfactant system including a primary surfactant selected from the group consisting of amphoteric surfactants and optionally a secondary surfactant selected from the group consisting of anionic surfactants;
   a volatile hydrocarbon solvent, wherein the volatile hydrocarbon solvent is selected from the group consisting of n-pentane, iso-pentane, $C_1$–$C_6$ alkyl ethers and mixtures thereof;

water; and an effective volatile hydrocarbon-solubilizing amount of a polyalkylene oxide block copolymer surfactant.

2. A composition as in claim 1 wherein the polyalkylene oxide block copolymer surfactant includes at least one polyethylene oxide block and at least one polypropylene oxide block.

3. A composition as in claim 1, wherein the polyalkylene oxide block copolymer is a triblock copolymer having a polypropylene oxide center block and polyethylene oxide end blocks.

4. A composition as in claim 1, wherein the polyalkylene oxide block copolymer is a triblock copolymer having an ethylene oxide center block and propylene oxide end blocks.

5. A composition as in claim 1, wherein the polyalkylene oxide block copolymer is of the formula:

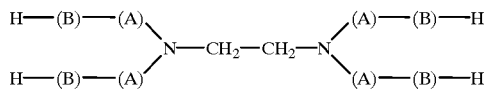

wherein A represents a block of propylene oxide repeating units and B represents a block of ethylene oxide repeating units.

6. A composition as in claim 1, wherein the polyalkylene oxide block copolymer is of the formula:

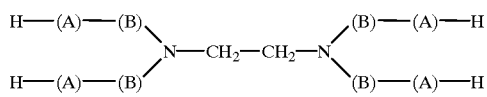

wherein A represents a block of propylene oxide repeating units and B represents a block of ethylene oxide repeating units.

7. A composition as in claim 1 wherein the surfactant system comprises an alkyl ether sulfate.

8. A compositions as in claim 1 wherein the volatile hydrocarbon solvent is present in an amount from about 1 to about 7 percent by weight of composition.

9. A composition as in claim 1 wherein the surfactant system comprises a betaine.

10. A composition as in claim 1 further comprising an active ingredient.

11. A composition as in claim 10 wherein the active ingredient is selected from the group consisting of triclosan, chlorohexidene gluconate and salycilic acid.

12. A composition comprising:
pentane;
water; and
an effective pentane-solubilizing amount of a surfactant system including an ammonium cocoyl isethionate and an amphoteric surfactant.

13. A composition as in claim 12 wherein the amphoteric surfactant is a betaine.

14. A composition as in claim 12 wherein the pentane is selected from the group consisting of n-pentane, iso-pentane, and combinations thereof.

15. A composition as in claim 12 wherein the pentane is present in an amount from about 1 to about 7 percent by weight of the composition.

16. A composition as in claim 13 wherein the betaine is selected from the group consisting of cocoamidopropyl betaine, behenyl betaine and babassuamidopropyl betaine.

17. A composition as in claim 12 further comprising an active ingredient.

18. A composition as in claim 17 wherein the active ingredient is selected from the group consisting of triclosan, chlorohexidene gluconate and salycilic acid.

19. A method for preventing separation of a volatile hydrocarbon from a surfactant system, the method comprising:

forming an aqueous solution containing one or more surfactants selected from the group consisting of anionic surfactants, amphoteric surfactants and combinations thereof and an effective volatile hydrocarbon-solubilizing amount of a polyalkylene oxide block copolymer surfactant;

mixing a volatile hydrocarbon solvent with the aqueous solution to form a clear solution or gel, wherein the volatile hydrocarbon solvent is selected from the group consisting of n-pentane, iso-pentane, $C_1$–$C_6$ alkyl ethers and mixtures thereof; and storing the clear solution or gel in a closed container.

20. A method of preventing separation of pentane from a surfactant system, the method comprising:

forming an aqueous solution containing an ammonium cocoyl isethionate and an amphoteric surfactant;

mixing pentane with the aqueous solution to form a clear solution or gel; and storing the clear solution or gel in a closed container.

* * * * *